United States Patent
Park et al.

(10) Patent No.: US 12,144,571 B2
(45) Date of Patent: Nov. 19, 2024

(54) FORCE TRANSMISSION SYSTEMS FOR ROBOTICALLY CONTROLLED MEDICAL DEVICES

(71) Applicant: EndoQuest Robotics, Inc., Houston, TX (US)

(72) Inventors: Yongman Park, Houston, TX (US); Daniel Kim, Houston, TX (US); Raymond Lee, Houston, TX (US); Sungwoo Cho, Houston, TX (US); Dongsuk Shin, Houston, TX (US)

(73) Assignee: EndoQuest Robotics, Inc., Houston, TX (US)

( * ) Notice: Subject to any disclaimer, the term of this patent is extended or adjusted under 35 U.S.C. 154(b) by 33 days.

(21) Appl. No.: 18/134,689

(22) Filed: Apr. 14, 2023

(65) Prior Publication Data
US 2023/0255702 A1   Aug. 17, 2023

Related U.S. Application Data

(63) Continuation of application No. PCT/US2022/051265, filed on Nov. 29, 2022.
(Continued)

(51) Int. Cl.
*A61B 17/00* (2006.01)
*A61B 34/00* (2016.01)
*A61B 34/30* (2016.01)

(52) U.S. Cl.
CPC .............. *A61B 34/30* (2016.02); *A61B 17/00* (2013.01); *A61B 34/71* (2016.02);
(Continued)

(58) Field of Classification Search
None
See application file for complete search history.

(56) References Cited

U.S. PATENT DOCUMENTS

| 5,792,135 A | 8/1998 | Madhani et al. |
| 5,797,900 A | 8/1998 | Madhani et al. |

(Continued)

FOREIGN PATENT DOCUMENTS

| CN | 105310775 A | 2/2016 |
| CN | 108309370 A | 7/2018 |

(Continued)

OTHER PUBLICATIONS

Culmone et al., Follow-The-Leader Mechanisms in Medical Devices: A Review on Scientific and Patent Literature, 2021, IEEE, p. 439-455 (Year: 2021).*

(Continued)

*Primary Examiner* — Mcdieunel Marc
(74) *Attorney, Agent, or Firm* — Locke Lord LLP; Scott D. Wofsy; Michael J. Pollack

(57) ABSTRACT

A force transmission system for a robotically controlled medical device can include a pushing actuator configured to be pushed by a robotic instrument controller and a wire. The wire can include a first end attached to an end of the pushing actuator to be pushed distally by the pushing actuator, and a second end attached to a distal location of the medical device. The system can include a reverse motion device that can be interfaced with the wire between the first end and the second end. The reverse motion device can be configured to cause a proximal pulling action on the second end in response to pushing of the first end distally by the pushing actuator or other actuation by the pushing actuator. The reverse motion device can be configured to maintain a point of contact with the wire in the same spatial location to prevent wire motion due to actuation.

18 Claims, 5 Drawing Sheets

Related U.S. Application Data

(60) Provisional application No. 63/284,298, filed on Nov. 30, 2021.

(52) U.S. Cl.
CPC ........ *A61B 2017/00323* (2013.01); *A61B 2017/00371* (2013.01); *A61B 2017/00398* (2013.01); *A61B 2034/301* (2016.02)

(56) References Cited

U.S. PATENT DOCUMENTS

| | | |
|---|---|---|
| 5,836,936 A | 11/1998 | Cuschieri |
| 5,976,122 A | 11/1999 | Madhani et al. |
| 6,063,095 A | 5/2000 | Wang et al. |
| 6,132,368 A | 10/2000 | Cooper |
| 6,162,239 A | 12/2000 | Manhes |
| 6,244,809 B1 | 6/2001 | Wang et al. |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,346,072 B1 | 2/2002 | Cooper |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,402,715 B2 | 6/2002 | Manhes |
| 6,424,885 B1 | 7/2002 | Niemeyer et al. |
| 6,441,577 B2 | 8/2002 | Blumenkranz et al. |
| 6,451,027 B1 | 9/2002 | Cooper et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,508,827 B1 | 1/2003 | Manhes |
| 6,522,906 B1 | 2/2003 | Salisbury, Jr. et al. |
| 6,565,554 B1 | 5/2003 | Niemeyer |
| 6,587,750 B2 | 7/2003 | Gerbi et al. |
| 6,645,196 B1 | 11/2003 | Nixon et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,699,177 B1 | 3/2004 | Wang et al. |
| 6,699,235 B2 | 3/2004 | Wallace et al. |
| 6,714,839 B2 | 3/2004 | Salisbury, Jr. et al. |
| 6,746,443 B1 | 6/2004 | Morley et al. |
| 6,766,204 B2 | 7/2004 | Niemeyer et al. |
| 6,783,524 B2 | 8/2004 | Anderson et al. |
| 6,785,593 B2 | 8/2004 | Wang et al. |
| 6,799,088 B2 | 9/2004 | Wang et al. |
| 6,817,972 B2 | 11/2004 | Snow |
| 6,817,974 B2 | 11/2004 | Cooper et al. |
| 6,836,703 B2 | 12/2004 | Wang et al. |
| 6,837,846 B2 | 1/2005 | Jaffe et al. |
| 6,840,938 B1 | 1/2005 | Morley et al. |
| 6,852,107 B2 | 2/2005 | Wang et al. |
| 6,866,671 B2 | 3/2005 | Tierney et al. |
| 6,871,117 B2 | 3/2005 | Wang et al. |
| 6,892,112 B2 | 5/2005 | Wang et al. |
| 6,905,491 B1 | 6/2005 | Wang et al. |
| 6,951,535 B2 | 10/2005 | Ghodoussi et al. |
| 6,991,627 B2 | 1/2006 | Madhani et al. |
| 6,994,703 B2 | 2/2006 | Wang et al. |
| 7,025,064 B2 | 4/2006 | Wang et al. |
| 7,027,892 B2 | 4/2006 | Wang et al. |
| 7,048,745 B2 | 5/2006 | Tierney et al. |
| 7,066,926 B2 | 6/2006 | Wallace et al. |
| 7,074,179 B2 | 7/2006 | Wang et al. |
| 7,083,571 B2 | 8/2006 | Wang et al. |
| 7,087,049 B2 | 8/2006 | Nowlin et al. |
| 7,090,637 B2 | 8/2006 | Danitz et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,204,844 B2 | 4/2007 | Jensen et al. |
| 7,276,065 B2 | 10/2007 | Morley et al. |
| 7,320,700 B2 | 1/2008 | Cooper et al. |
| 7,326,228 B2 | 2/2008 | Cuschieri et al. |
| 7,331,967 B2 | 2/2008 | Lee et al. |
| 7,333,642 B2 | 2/2008 | Green |
| 7,357,774 B2 | 4/2008 | Cooper |
| 7,398,707 B2 | 7/2008 | Morley et al. |
| 7,524,320 B2 | 4/2009 | Tierney et al. |
| 7,553,277 B2 | 6/2009 | Hoefig et al. |
| 7,574,250 B2 | 8/2009 | Niemeyer |
| 7,608,083 B2 | 10/2009 | Lee et al. |
| 7,615,066 B2 | 11/2009 | Danitz et al. |
| 7,691,098 B2 | 4/2010 | Wallace et al. |
| 7,744,608 B2 | 6/2010 | Lee et al. |
| 7,756,036 B2 | 7/2010 | Druke et al. |
| 7,757,028 B2 | 7/2010 | Druke et al. |
| 7,763,015 B2 | 7/2010 | Cooper et al. |
| 7,780,651 B2 | 8/2010 | Madhani et al. |
| 7,837,674 B2 | 11/2010 | Cooper |
| 7,854,738 B2 | 12/2010 | Lee et al. |
| 7,865,266 B2 | 1/2011 | Moll et al. |
| 7,955,322 B2 | 6/2011 | Devengenzo et al. |
| 7,967,746 B2 | 6/2011 | Leroy et al. |
| 8,052,636 B2 | 11/2011 | Moll et al. |
| 8,054,752 B2 | 11/2011 | Druke et al. |
| 8,068,649 B2 | 11/2011 | Green |
| 8,075,474 B2 | 12/2011 | Honda et al. |
| 8,100,133 B2 | 1/2012 | Mintz et al. |
| 8,120,301 B2 | 2/2012 | Goldberg et al. |
| 8,123,740 B2 | 2/2012 | Madhani et al. |
| 8,147,503 B2 | 4/2012 | Zhao et al. |
| 8,169,468 B2 | 5/2012 | Scott et al. |
| 8,182,415 B2 | 5/2012 | Larkin et al. |
| 8,190,238 B2 | 5/2012 | Moll et al. |
| 8,228,368 B2 | 7/2012 | Zhao et al. |
| 8,323,297 B2 | 12/2012 | Hinman et al. |
| 8,335,590 B2 | 12/2012 | Costa et al. |
| 8,337,521 B2 | 12/2012 | Cooper et al. |
| 8,343,045 B2 | 1/2013 | Swinehart et al. |
| 8,343,141 B2 | 1/2013 | Madhani et al. |
| 8,365,633 B2 | 2/2013 | Simaan et al. |
| 8,375,808 B2 | 2/2013 | Blumenkranz et al. |
| 8,398,541 B2 | 3/2013 | DiMaio et al. |
| 8,437,629 B2 | 5/2013 | McDowall |
| 8,469,947 B2 | 6/2013 | Devengenzo et al. |
| 8,475,366 B2 | 7/2013 | Boulais et al. |
| 8,506,555 B2 | 8/2013 | Ruiz Morales |
| 8,591,399 B2 | 11/2013 | Marescaux et al. |
| 8,594,841 B2 | 11/2013 | Zhao et al. |
| 8,597,280 B2 | 12/2013 | Cooper et al. |
| 8,600,551 B2 | 12/2013 | Itkowitz et al. |
| 8,617,102 B2 | 12/2013 | Moll et al. |
| 8,644,988 B2 | 2/2014 | Prisco et al. |
| 8,679,099 B2 | 3/2014 | Cooper et al. |
| 8,690,908 B2 | 4/2014 | Cooper et al. |
| 8,709,000 B2 | 4/2014 | Madhani et al. |
| 8,740,885 B2 | 6/2014 | Larkin et al. |
| 8,784,435 B2 | 7/2014 | Cooper et al. |
| 8,786,241 B2 | 7/2014 | Nowlin et al. |
| 8,790,243 B2 | 7/2014 | Cooper et al. |
| 8,801,661 B2 | 8/2014 | Moll et al. |
| 8,810,631 B2 | 8/2014 | Scott et al. |
| 8,816,628 B2 | 8/2014 | Nowlin et al. |
| 8,821,480 B2 | 9/2014 | Burbank |
| 8,831,782 B2 | 9/2014 | Itkowitz |
| 8,838,270 B2 | 9/2014 | Druke et al. |
| 8,852,208 B2 | 10/2014 | Gomez et al. |
| 8,878,920 B2 | 11/2014 | Ovod |
| 8,887,595 B2 | 11/2014 | Williams |
| 8,888,690 B2 | 11/2014 | Swinehart et al. |
| 8,888,764 B2 | 11/2014 | Devengenzo et al. |
| 8,903,549 B2 | 12/2014 | Itkowitz et al. |
| 8,918,207 B2 | 12/2014 | Prisco |
| 8,944,070 B2 | 2/2015 | Guthart et al. |
| 8,945,095 B2 | 2/2015 | Blumenkranz et al. |
| 8,960,520 B2 * | 2/2015 | McCuen .......... A61B 17/068 227/175.1 |
| 8,998,797 B2 | 4/2015 | Omori |
| 9,011,318 B2 | 4/2015 | Choset et al. |
| 9,050,120 B2 | 6/2015 | Swarup et al. |
| 9,060,678 B2 | 6/2015 | Larkin et al. |

(56) References Cited

U.S. PATENT DOCUMENTS

| | | | |
|---|---|---|---|
| 9,089,354 B2 | 7/2015 | Simaan et al. | |
| 9,095,362 B2 | 8/2015 | Dachs, II et al. | |
| 9,107,572 B2 | 8/2015 | Marescaux et al. | |
| 9,138,284 B2 | 9/2015 | Krom et al. | |
| 9,144,456 B2 | 9/2015 | Rosa et al. | |
| 9,161,817 B2 * | 10/2015 | Olson | A61B 34/77 |
| 9,173,548 B2 | 11/2015 | Omori | |
| 9,179,979 B2 | 11/2015 | Jinno | |
| 9,186,221 B2 | 11/2015 | Burbank | |
| 9,254,090 B2 | 2/2016 | Watson et al. | |
| 9,259,274 B2 | 2/2016 | Prisco | |
| 9,259,276 B2 | 2/2016 | Mintz et al. | |
| 9,301,807 B2 | 4/2016 | Duval | |
| 9,308,937 B2 | 4/2016 | Griffiths et al. | |
| 9,339,341 B2 | 5/2016 | Cooper | |
| 9,358,074 B2 | 6/2016 | Schena et al. | |
| 9,433,342 B2 | 9/2016 | Perretta et al. | |
| 9,456,839 B2 | 10/2016 | Cooper | |
| 9,486,288 B2 | 11/2016 | Devengenzo et al. | |
| 9,498,242 B2 | 11/2016 | Crews et al. | |
| 9,504,517 B2 | 11/2016 | Rosa et al. | |
| 9,510,915 B2 | 12/2016 | Madhani et al. | |
| 9,531,699 B2 | 12/2016 | Panchura et al. | |
| 9,554,827 B2 | 1/2017 | Omori | |
| 9,565,990 B2 | 2/2017 | Lee et al. | |
| 9,596,980 B2 | 3/2017 | Marescaux et al. | |
| 9,687,310 B2 | 6/2017 | Nowlin et al. | |
| 9,717,486 B2 | 8/2017 | Cooper et al. | |
| 9,757,149 B2 | 9/2017 | Cooper et al. | |
| 9,757,203 B2 | 9/2017 | Hourtash et al. | |
| 9,775,678 B2 | 10/2017 | Lohmeier | |
| 9,782,056 B2 | 10/2017 | McDowall | |
| 9,782,225 B2 | 10/2017 | Lohmeier et al. | |
| 9,795,446 B2 | 10/2017 | DiMaio et al. | |
| 9,795,453 B2 | 10/2017 | Tierney et al. | |
| 9,801,526 B2 | 10/2017 | Larkin et al. | |
| 9,801,654 B2 | 10/2017 | Gomez et al. | |
| 9,814,527 B2 | 11/2017 | Rogers et al. | |
| 9,867,603 B2 | 1/2018 | Merz et al. | |
| 9,877,794 B2 | 1/2018 | Csiky | |
| 9,901,402 B2 | 2/2018 | Itkowitz et al. | |
| 9,918,659 B2 | 3/2018 | Chopra et al. | |
| 9,949,620 B2 | 4/2018 | Duval et al. | |
| 9,962,066 B2 | 5/2018 | Rogers et al. | |
| 9,968,405 B2 | 5/2018 | Cooper et al. | |
| 9,980,630 B2 | 5/2018 | Larkin et al. | |
| 10,010,331 B2 | 7/2018 | Morash | |
| 10,039,473 B2 | 8/2018 | Zhao et al. | |
| 10,058,390 B2 | 8/2018 | Simaan et al. | |
| 10,085,788 B2 | 10/2018 | Privitera et al. | |
| 10,085,806 B2 | 10/2018 | Hagn et al. | |
| 10,092,172 B2 | 10/2018 | Peh et al. | |
| 10,105,128 B2 | 10/2018 | Cooper et al. | |
| 10,117,715 B2 | 11/2018 | Lohmeier et al. | |
| 10,159,536 B2 | 12/2018 | Kralicky et al. | |
| 10,178,368 B2 | 1/2019 | Zhao et al. | |
| 10,179,024 B2 | 1/2019 | Yeung | |
| 10,179,413 B2 | 1/2019 | Rockrohr | |
| 10,188,472 B2 | 1/2019 | Diolaiti et al. | |
| 10,258,421 B2 | 4/2019 | Lohmeier et al. | |
| 10,278,782 B2 | 5/2019 | Jarc et al. | |
| 10,321,964 B2 | 6/2019 | Grover et al. | |
| 10,327,856 B2 | 6/2019 | Kralicky et al. | |
| 10,363,107 B2 | 7/2019 | Blumenkranz et al. | |
| 10,365,295 B2 | 7/2019 | Blumenkranz et al. | |
| 10,390,687 B2 | 8/2019 | Choi et al. | |
| 10,390,895 B2 | 8/2019 | Henderson et al. | |
| 10,391,635 B2 | 8/2019 | Berghofer et al. | |
| 10,398,520 B2 | 9/2019 | Larkin et al. | |
| 10,413,370 B2 | 9/2019 | Yates et al. | |
| 10,448,813 B2 | 10/2019 | Cooper et al. | |
| 10,456,166 B2 | 10/2019 | Cooper et al. | |
| 10,507,068 B2 | 12/2019 | Kopp et al. | |
| 10,512,481 B2 | 12/2019 | Cooper | |
| 10,524,644 B2 | 1/2020 | Scott et al. | |
| 10,524,868 B2 | 1/2020 | Cooper et al. | |
| 10,525,236 B2 * | 1/2020 | Belson | A61B 5/150389 |
| 10,531,929 B2 | 1/2020 | Widenhouse et al. | |
| 10,602,958 B2 | 3/2020 | Silverstein et al. | |
| 10,646,990 B2 | 5/2020 | Olds et al. | |
| 10,660,713 B2 | 5/2020 | McCrea et al. | |
| 10,682,193 B2 | 6/2020 | Choi et al. | |
| 10,729,503 B2 | 8/2020 | Cameron | |
| 10,736,702 B2 | 8/2020 | Harris et al. | |
| 10,779,896 B2 | 9/2020 | Dachs, II et al. | |
| 10,779,899 B2 | 9/2020 | Griffiths et al. | |
| 10,786,329 B2 | 9/2020 | Schuh et al. | |
| 10,820,953 B2 | 11/2020 | Kralicky et al. | |
| 10,828,115 B2 | 11/2020 | Koenig et al. | |
| 10,828,117 B2 | 11/2020 | Evans | |
| 10,835,331 B2 | 11/2020 | Burbank | |
| 10,835,335 B2 | 11/2020 | Perdue et al. | |
| 10,856,946 B2 | 12/2020 | Solomon et al. | |
| 10,864,051 B2 | 12/2020 | Simi et al. | |
| 10,874,475 B2 | 12/2020 | Iceman | |
| 10,881,422 B2 | 1/2021 | Kim et al. | |
| 10,898,189 B2 | 1/2021 | McDonald, II | |
| 10,898,281 B2 | 1/2021 | Cooper et al. | |
| 10,905,505 B1 | 2/2021 | Barakat et al. | |
| 10,918,449 B2 | 2/2021 | Solomon et al. | |
| 10,939,970 B2 | 3/2021 | Laakso et al. | |
| 10,959,607 B2 | 3/2021 | Rogers et al. | |
| 11,278,703 B2 * | 3/2022 | Kokish | A61M 25/0113 |
| 11,730,349 B2 * | 8/2023 | Altshuler | A61B 1/0057 600/114 |
| 2002/0161281 A1 | 10/2002 | Jaffe et al. | |
| 2003/0036748 A1 | 2/2003 | Cooper et al. | |
| 2003/0083673 A1 | 5/2003 | Tierney et al. | |
| 2003/0114962 A1 | 6/2003 | Niemeyer | |
| 2003/0135203 A1 | 7/2003 | Wang et al. | |
| 2004/0049205 A1 | 3/2004 | Lee et al. | |
| 2004/0138700 A1 | 7/2004 | Cooper et al. | |
| 2004/0162547 A1 | 8/2004 | Wallace et al. | |
| 2004/0236316 A1 | 11/2004 | Danitz et al. | |
| 2005/0043718 A1 | 2/2005 | Madhani et al. | |
| 2005/0059960 A1 | 3/2005 | Simaan et al. | |
| 2005/0149003 A1 | 7/2005 | Tierney et al. | |
| 2005/0200324 A1 | 9/2005 | Guthart et al. | |
| 2005/0204851 A1 | 9/2005 | Morley et al. | |
| 2005/0216033 A1 | 9/2005 | Lee et al. | |
| 2005/0251112 A1 | 11/2005 | Danitz et al. | |
| 2006/0152516 A1 | 7/2006 | Plummer | |
| 2006/0167440 A1 | 7/2006 | Cooper et al. | |
| 2007/0043338 A1 | 2/2007 | Moll et al. | |
| 2007/0137372 A1 | 6/2007 | Devengenzo et al. | |
| 2007/0151390 A1 | 7/2007 | Blumenkranz et al. | |
| 2007/0156119 A1 | 7/2007 | Wallace et al. | |
| 2007/0156122 A1 | 7/2007 | Cooper | |
| 2007/0197896 A1 | 8/2007 | Moll et al. | |
| 2007/0244515 A1 | 10/2007 | Fanous | |
| 2008/0065105 A1 | 3/2008 | Larkin et al. | |
| 2008/0065107 A1 | 3/2008 | Larkin et al. | |
| 2008/0065111 A1 | 3/2008 | Blumenkranz et al. | |
| 2008/0071291 A1 | 3/2008 | Duval et al. | |
| 2008/0077159 A1 | 3/2008 | Madhani et al. | |
| 2008/0177282 A1 | 7/2008 | Lee et al. | |
| 2008/0177284 A1 | 7/2008 | Lee et al. | |
| 2008/0269562 A1 | 10/2008 | Marescaux et al. | |
| 2008/0287963 A1 | 11/2008 | Rogers et al. | |
| 2009/0023989 A1 | 1/2009 | Honda et al. | |
| 2009/0171151 A1 | 7/2009 | Choset et al. | |
| 2009/0192519 A1 | 7/2009 | Omori | |
| 2010/0011901 A1 | 1/2010 | Burbank | |
| 2010/0048999 A1 | 2/2010 | Boulais et al. | |
| 2010/0082041 A1 | 4/2010 | Prisco | |
| 2010/0234831 A1 | 9/2010 | Hinman et al. | |
| 2010/0274087 A1 | 10/2010 | Diolaiti et al. | |
| 2010/0292708 A1 | 11/2010 | Madhani et al. | |
| 2011/0118755 A1 | 5/2011 | Cooper et al. | |
| 2011/0125166 A1 | 5/2011 | Cooper et al. | |
| 2011/0144658 A1 | 6/2011 | Wenderow et al. | |
| 2011/0152879 A1 | 6/2011 | Williams | |
| 2011/0196419 A1 | 8/2011 | Cooper | |
| 2011/0277580 A1 | 11/2011 | Cooper et al. | |

(56) References Cited

U.S. PATENT DOCUMENTS

| | | |
|---|---|---|
| 2011/0282351 A1 | 11/2011 | Cooper et al. |
| 2011/0282359 A1 | 11/2011 | Duval |
| 2011/0282491 A1 | 11/2011 | Prisco et al. |
| 2011/0288561 A1 | 11/2011 | Devengenzo et al. |
| 2011/0313449 A1 | 12/2011 | Cooper |
| 2012/0150192 A1 | 6/2012 | Dachs, II et al. |
| 2012/0203271 A1 | 8/2012 | Larkin et al. |
| 2012/0209174 A1 | 8/2012 | Moll et al. |
| 2012/0221011 A1 | 8/2012 | Larkin et al. |
| 2012/0232339 A1 | 9/2012 | Csiky |
| 2013/0053868 A1 | 2/2013 | Cooper et al. |
| 2013/0079794 A9 | 3/2013 | Cooper et al. |
| 2013/0096540 A1 | 4/2013 | Cooper et al. |
| 2013/0110131 A1 | 5/2013 | Madhani et al. |
| 2013/0123800 A1 | 5/2013 | Leroy et al. |
| 2013/0197539 A1 | 8/2013 | Simaan et al. |
| 2013/0197540 A1 | 8/2013 | Simaan et al. |
| 2013/0267950 A1 | 10/2013 | Rosa et al. |
| 2013/0267964 A1 | 10/2013 | Rogers et al. |
| 2013/0274761 A1 | 10/2013 | Devengenzo et al. |
| 2014/0081292 A1 | 3/2014 | Moll et al. |
| 2014/0194899 A1 | 7/2014 | Madhani et al. |
| 2014/0243852 A1 | 8/2014 | Cooper et al. |
| 2014/0257336 A1 | 9/2014 | Choi et al. |
| 2014/0277106 A1 | 9/2014 | Crews et al. |
| 2014/0296637 A1 | 10/2014 | Lee et al. |
| 2014/0296872 A1 | 10/2014 | Cooper et al. |
| 2015/0066002 A1 | 3/2015 | Cooper et al. |
| 2015/0100066 A1 | 4/2015 | Kostrzewski et al. |
| 2015/0150636 A1 | 6/2015 | Hagn et al. |
| 2015/0173726 A1 | 6/2015 | Lohmeier et al. |
| 2015/0173729 A1 | 6/2015 | Lohmeier et al. |
| 2015/0173731 A1 | 6/2015 | Lohmeier et al. |
| 2015/0173840 A1 | 6/2015 | Lohmeier |
| 2015/0238267 A1 | 8/2015 | Devengenzo et al. |
| 2015/0250546 A1 | 9/2015 | Larkin et al. |
| 2016/0015447 A1 | 1/2016 | Rosa et al. |
| 2016/0058512 A1 | 3/2016 | Gomez et al. |
| 2016/0066773 A1 | 3/2016 | Cooper et al. |
| 2016/0242860 A1 | 8/2016 | Diolaiti et al. |
| 2016/0256183 A1 | 9/2016 | Cooper |
| 2017/0014197 A1 | 1/2017 | McCrea et al. |
| 2017/0020615 A1 | 1/2017 | Koenig et al. |
| 2017/0071628 A1 | 3/2017 | Cooper et al. |
| 2017/0112505 A1 | 4/2017 | Morash |
| 2017/0156804 A1 | 6/2017 | Cooper et al. |
| 2017/0265923 A1 | 9/2017 | Privitera et al. |
| 2017/0273749 A1 | 9/2017 | Grover et al. |
| 2017/0274533 A1 | 9/2017 | Berghofer et al. |
| 2017/0281296 A1 | 10/2017 | Cooper et al. |
| 2017/0312043 A1 | 11/2017 | Ogawa et al. |
| 2017/0325879 A1 | 11/2017 | Yeung |
| 2017/0354318 A1 | 12/2017 | Rogers et al. |
| 2017/0367775 A1 | 12/2017 | Dachs, II et al. |
| 2017/0367777 A1 | 12/2017 | Kralicky et al. |
| 2018/0000318 A9 | 1/2018 | Rogers et al. |
| 2018/0000548 A1 | 1/2018 | Olds et al. |
| 2018/0014852 A1 | 1/2018 | Gomez et al. |
| 2018/0049820 A1 | 2/2018 | Widenhouse et al. |
| 2018/0049822 A1 | 2/2018 | Henderson et al. |
| 2018/0049827 A1 | 2/2018 | Harris et al. |
| 2018/0064498 A1 | 3/2018 | Kapadia et al. |
| 2018/0111273 A1 | 4/2018 | Linnell et al. |
| 2018/0132956 A1 | 5/2018 | Cameron |
| 2018/0168747 A1 | 6/2018 | Kopp et al. |
| 2018/0168752 A1 | 6/2018 | Scheib et al. |
| 2018/0193007 A1 | 7/2018 | Au et al. |
| 2018/0200894 A1 | 7/2018 | Rockrohr |
| 2018/0214176 A1 | 8/2018 | Solomon et al. |
| 2018/0221096 A1 | 8/2018 | Yates et al. |
| 2018/0242824 A1 | 8/2018 | Larkin et al. |
| 2018/0256270 A1 | 9/2018 | Cooper et al. |
| 2018/0271607 A1 | 9/2018 | Kralicky et al. |
| 2018/0271616 A1 | 9/2018 | Schuh et al. |
| 2018/0286287 A1 | 10/2018 | Razzaque |
| 2018/0296299 A1 | 10/2018 | Iceman |
| 2018/0317915 A1 | 11/2018 | McDonald, II |
| 2018/0318023 A1 | 11/2018 | Griffiths et al. |
| 2018/0353204 A1 | 12/2018 | Solomon et al. |
| 2018/0370045 A1 | 12/2018 | Kan |
| 2019/0039241 A1 | 2/2019 | Langenfeld et al. |
| 2019/0117247 A1 | 4/2019 | Kim et al. |
| 2019/0125467 A1 | 5/2019 | Evans |
| 2019/0216551 A1 | 7/2019 | Burbank |
| 2019/0269472 A1 | 9/2019 | Kralicky et al. |
| 2019/0274769 A1 | 9/2019 | Perdue et al. |
| 2019/0314645 A1 | 10/2019 | Ciresianu et al. |
| 2019/0328472 A1 | 10/2019 | Tojo et al. |
| 2019/0380801 A1 | 12/2019 | Savall et al. |
| 2020/0038123 A1 | 2/2020 | Graetzel et al. |
| 2020/0069389 A1 | 3/2020 | Morrissette et al. |
| 2020/0107898 A1 | 4/2020 | Kim et al. |
| 2020/0146763 A1 | 5/2020 | Schena et al. |
| 2020/0179067 A1 | 6/2020 | Ross et al. |
| 2020/0205917 A1 | 7/2020 | Peine et al. |
| 2020/0214774 A1 | 7/2020 | Yoshida et al. |
| 2020/0297444 A1 | 9/2020 | Camarillo et al. |
| 2020/0330173 A1 | 10/2020 | Kapadia et al. |
| 2020/0345645 A1 | 11/2020 | Saiki et al. |
| 2020/0367979 A1 | 11/2020 | Laakso et al. |
| 2020/0397456 A1 | 12/2020 | Kim et al. |
| 2020/0397457 A1 | 12/2020 | Kim et al. |
| 2021/0045819 A1 | 2/2021 | Castillo et al. |
| 2021/0241542 A1 | 8/2021 | Shmayahu et al. |
| 2021/0259794 A1 | 8/2021 | Kato et al. |
| 2021/0267702 A1 | 9/2021 | Kim et al. |
| 2021/0275266 A1 | 9/2021 | Kim et al. |
| 2021/0322045 A1 | 10/2021 | Kim et al. |
| 2021/0322046 A1 | 10/2021 | Kim et al. |
| 2021/0338052 A1 | 11/2021 | Ouyang et al. |
| 2022/0354524 A1 | 11/2022 | Kim et al. |
| 2023/0210618 A1 | 7/2023 | Kim et al. |
| 2023/0210621 A1 | 7/2023 | Noh et al. |
| 2023/0248419 A1 | 8/2023 | Cho et al. |
| 2023/0248450 A1 | 8/2023 | Ravi et al. |
| 2023/0248457 A1 | 8/2023 | Lee et al. |
| 2023/0285090 A1 | 9/2023 | Lee et al. |
| 2023/0285098 A1 | 9/2023 | Lee et al. |
| 2023/0285099 A1 | 9/2023 | Lee et al. |
| 2023/0355221 A1 | 11/2023 | Shin et al. |
| 2023/0363842 A1 | 11/2023 | Choi et al. |
| 2023/0363847 A1 | 11/2023 | Lee et al. |
| 2024/0058079 A1 | 2/2024 | Kim et al. |

FOREIGN PATENT DOCUMENTS

| | | |
|---|---|---|
| CN | 109674647 A | 4/2019 |
| CN | 213606867 U | 7/2021 |
| EP | 2968048 B1 | 6/2018 |
| EP | 3175813 B1 | 1/2020 |
| JP | 2019530517 A | 10/2019 |
| JP | 2020104843 A | 7/2020 |
| JP | 2021513442 A | 5/2021 |
| KR | 20110032444 A | 3/2011 |
| KR | 101943440 B1 | 1/2019 |
| TW | 200808255 A | 2/2008 |
| WO | 2012/035492 A1 | 3/2012 |
| WO | 2016/109886 A1 | 7/2016 |
| WO | 2019055681 A1 | 3/2019 |
| WO | 2020243285 A1 | 12/2020 |
| WO | 2021026231 A1 | 2/2021 |
| WO | 2021071540 A1 | 4/2021 |
| WO | 2021161162 A1 | 8/2021 |
| WO | 2021161184 A1 | 8/2021 |

OTHER PUBLICATIONS

Choi et al., Exo-Wrist: A Soft Tendon-Driven Wrist-Wearable Robot With Active Anchor for Dart-Throwing Motion in Hemiplegic Patients, 2019, IEEE, p. 4499-4506 (Year: 2019).*

Ahmed et al., Characterization of a Screw-Based Bending Actuator for Continuum Robots, 2020, IEEE, p. 89-95 (Year: 2020).*

(56) References Cited

OTHER PUBLICATIONS

Ali et al., Steerable Catheters in Cardiology: Classifying Steerability and Assessing Future Challenges, 2016, IEEE, p. 679-693 (Year: 2016).*
"Plenary 1: Colubris MX"—YouTube Video link address https://www.youtube.com/watch?v=in_luQiAZg8 dated Aug. 20, 2020.
International Search Report and Written Opinion, of the Korean Intellectual Property Office, as ISA, mailed Apr. 6, 2023, in corresponding International Patent Application PCT/US2022/051217.
International Search Report and Written Opinion, of the Korean Intellectual Property Office, as ISA, mailed Apr. 6, 2023, in corresponding International Patent Application PCT/US2022/051220.
International Search Report and Written Opinion, of the Korean Intellectual Property Office, as ISA, mailed Apr. 7, 2023, in corresponding International Patent Application PCT/US2022/051225.
International Search Report and Written Opinion, of the Korean Intellectual Property Office, as ISA, mailed Apr. 6, 2023, in corresponding International Patent Application PCT/US2022/051237.
International Search Report and Written Opinion, of the Korean Intellectual Property Office, as ISA, mailed Apr. 6, 2023, in corresponding International Patent Application PCT/US2022/051246.
International Search Report and Written Opinion, of the Korean Intellectual Property Office, as ISA, mailed Apr. 6, 2023, in corresponding International Patent Application PCT/US2022/051255.
International Search Report and Written Opinion, of the Korean Intellectual Property Office, as ISA, mailed Apr. 6, 2023, in corresponding International Patent Application PCT/US2022/051259.
International Search Report and Written Opinion, of the Korean Intellectual Property Office, as ISA, mailed Apr. 6, 2023, in corresponding International Patent Application PCT/US2022/051261.
International Search Report and Written Opinion, of the Korean Intellectual Property Office, as ISA, mailed Apr. 14, 2023, in corresponding International Patent Application PCT/US2022/051265.
International Search Report and Written Opinion, of the Korean Intellectual Property Office, as ISA, mailed Apr. 6, 2023, in corresponding International Patent Application PCT/US2022/051262.
Taiwan Intellectual Property Office, Office Action and Search Report issued on Jun. 13, 2024, in corresponding Taiwan Invention Patent Application No. 111145615.
International Search Report and Written Opinion, of the Korean Intellectual Property Office, as ISA, mailed Apr. 14, 2023, in corresponding International Patent Application PCT/US22/051265.

* cited by examiner

FORCE TRANSMISSION SYSTEMS FOR ROBOTICALLY CONTROLLED MEDICAL DEVICES

CROSS-REFERENCE TO RELATED APPLICATIONS

This application is a continuation of International Patent Application No. PCT/US2022/051265 filed Nov. 29, 2022, which claims priority to and the benefit of U.S. Provisional Application No. 63/284,298, filed Nov. 30, 2021, the entire contents of which are herein incorporated by reference in their entirety.

FIELD

This disclosure relates to robotic surgical systems, e.g., for minimally invasive surgery including, but not limited to, endoluminal and single-site surgery.

BACKGROUND

Minimally invasive surgery such as endoluminal and single-site robotic surgery offer significant advantages versus traditional robotic surgery. For example, in endoluminal robotic surgery, no incision need be made to access difficult to access locations within a patient's natural lumen. This dramatically reduces and/or eliminates recovery time and improves procedural safety. A single-site system reduces incisions to a minimum single-site, which reduces an otherwise larger number of incisions to provide access for certain procedures.

Certain endoluminal and single-site robotic surgical systems have been proposed. Examples of such systems and related components can be found in U.S. Pat. No. 10,881,422, as well as U.S. Patent Application Nos. US20210322046, US20210322045, US20190117247, US20210275266, US20210267702, US20200107898, US20200397457, US202000397456, US20200315645, and US201962914226, all of the above being incorporated by reference herein in their entirety.

Conventional surgical robotics and systems have generally been considered satisfactory for their intended purpose. However, there is still a need in the art for improved robotic surgical systems, devices, methods, controls, and components, especially those configured for endoluminal and single-site surgery. The present disclosure provides improvements in such areas, for example.

SUMMARY

In accordance with at least one aspect of this disclosure, a force transmission system for a robotically controlled medical device can include a pushing actuator configured to be pushed by a robotic instrument controller and a wire. The wire can include a first end attached to an end of the pushing actuator to be pushed distally by the pushing actuator attached to a location that moves with movement of the pushing actuator, and a second end attached to a distal location of the medical device. The system can include a reverse motion device that can be interfaced with the wire between the first end and the second end. The reverse motion device can be configured to cause a proximal pulling action on the second end in response to pushing of the first end distally by the pushing actuator or other actuation by the pushing actuator. The reverse motion device can be configured to maintain a point of contact with the wire in the same spatial location to prevent wire motion due to actuation.

In certain embodiments, the reverse motion device can be one or more pulleys rotatably mounted and axially fixed to a base. The one or more pulleys can be interfaced with the wire. The pushing actuator can be configured to move axially relative to the base to push the wire.

In certain embodiments, the one or more pulleys can include a first pulley and a second pulley configured to reverse direction of the wire. In certain embodiments, the first pulley can be inserted within a slot of the pushing actuator to cause the wire to contact the first pulley such that the wire is parallel and/or coaxial with a pushing axis. The second pulley can be sized and/or positioned to contact the wire to be coaxial with a proximal direction axis. The second pulley can be larger than the first pulley. In certain embodiments, the reverse direction of the wire can be 180 degrees.

In certain embodiments, the reverse motion device can be a reverse linkage attached to the pushing actuator on a first end and interfaced with a wire on the second end. The reverse linkage can be rotatably mounted and axially fixed to a base. The second end of the reverse linkage can be or include a curved contact surface to maintain the point of contact with the wire in the same spatial location to prevent wire motion due to actuation.

In accordance with at least one aspect of this disclosure, a force transmission system for a robotically controlled medical device can include a pushing actuator configured to be pushed by a robotic instrument controller, and one or more pulleys mounted relative to the pushing actuator. The system can include a wire having a first end attached to an end of the pushing actuator to be pushed distally by the pushing actuator, and a second end attached to a distal location of the medical device. The wire can be interfaced with the one or more pulleys to cause a proximal pulling action on the second end in response to pushing of the first end distally.

In accordance with at least one aspect of this disclosure, a robotically controlled medical device can include a steerable elongate member and a hub (e.g., connected to the steerable elongate member. The medical device can include a force transmission system disposed in the hub. The force transmission system can be or include any suitable force transmission system disclosed herein, e.g., as described above.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1A:
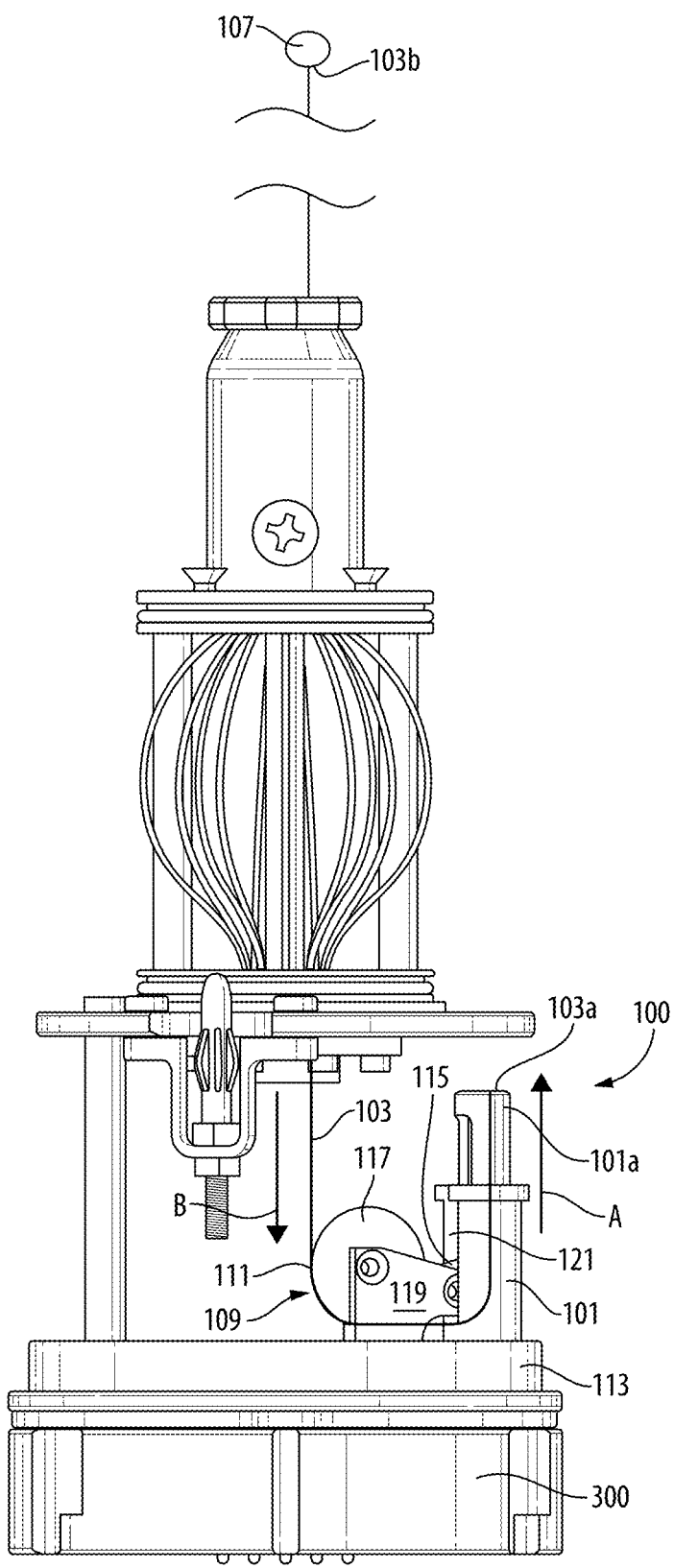
FIG. 1A is an elevation view of an embodiment of a force transmission system in accordance with this disclosure.
Figure 1B:
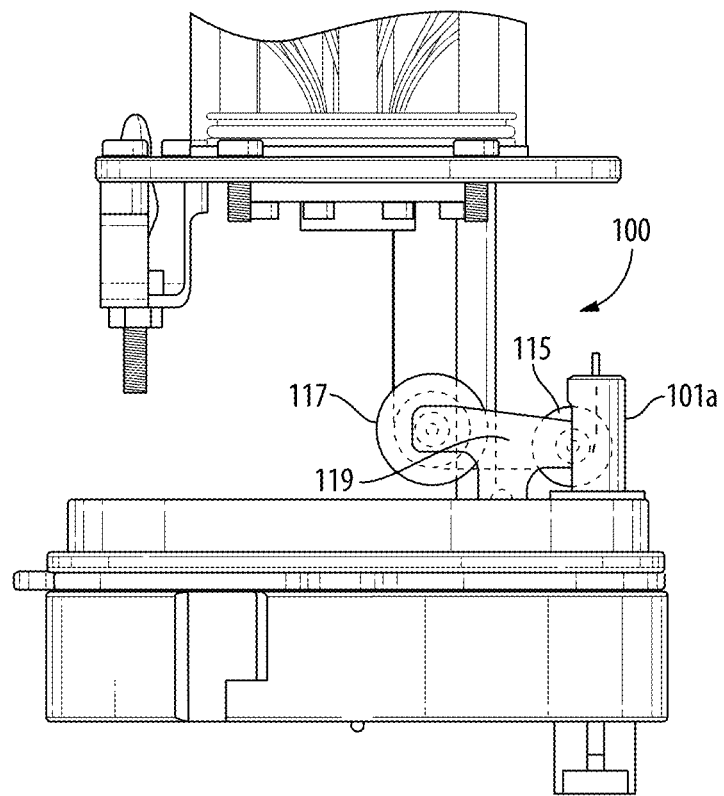
FIG. 1B is an elevation view of the embodiment of FIG. 1A, shown having the actuator shown in phantom to illustrate the pulley assembly in a retracted position.
Figure 1C:
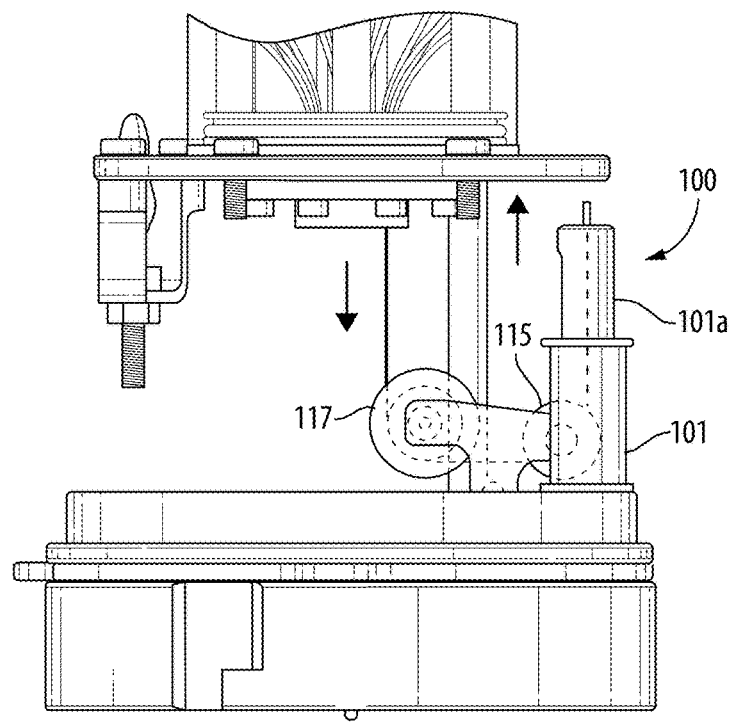
FIG. 1C is an elevation view of the embodiment of FIG. 1A, shown having the actuator extended.
Figure 1D:
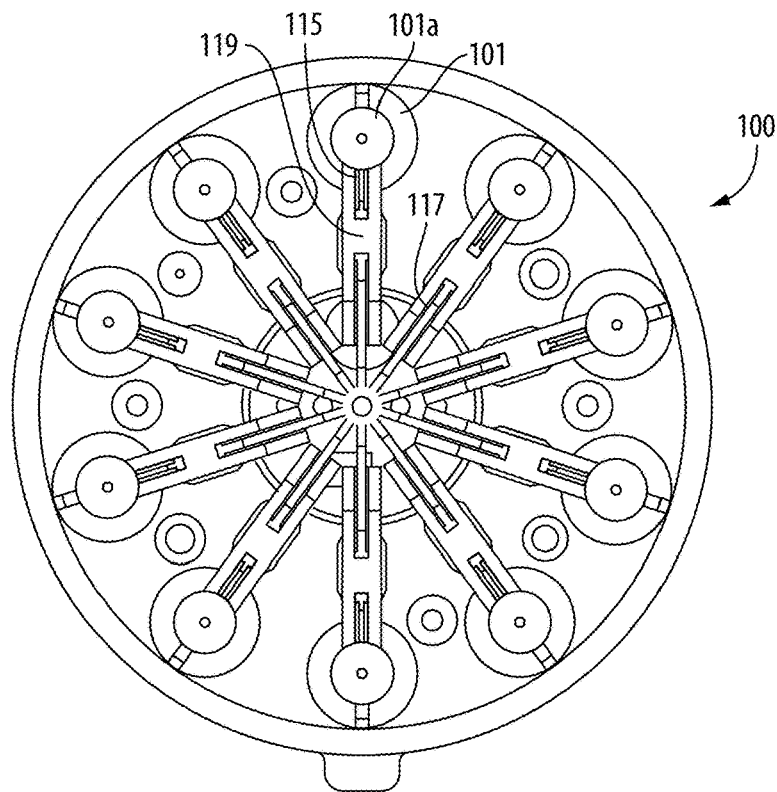
FIG. 1D is a plan view of the embodiment of FIG. 1A showing a plurality of pulley assemblies and actuators configured to actuate a plurality of cables.

Reference will now be made to the drawings wherein like reference numerals identify similar structural features or aspects of the subject disclosure. For purposes of explanation and illustration, and not limitation, an illustrative view of an embodiment of a force transmission system in accordance with the disclosure is shown in FIGS. 1A and 1s designated generally by reference character 100. Other embodiments and/or aspects of this disclosure are shown in FIGS. 1B-2B.

Figure 2A:
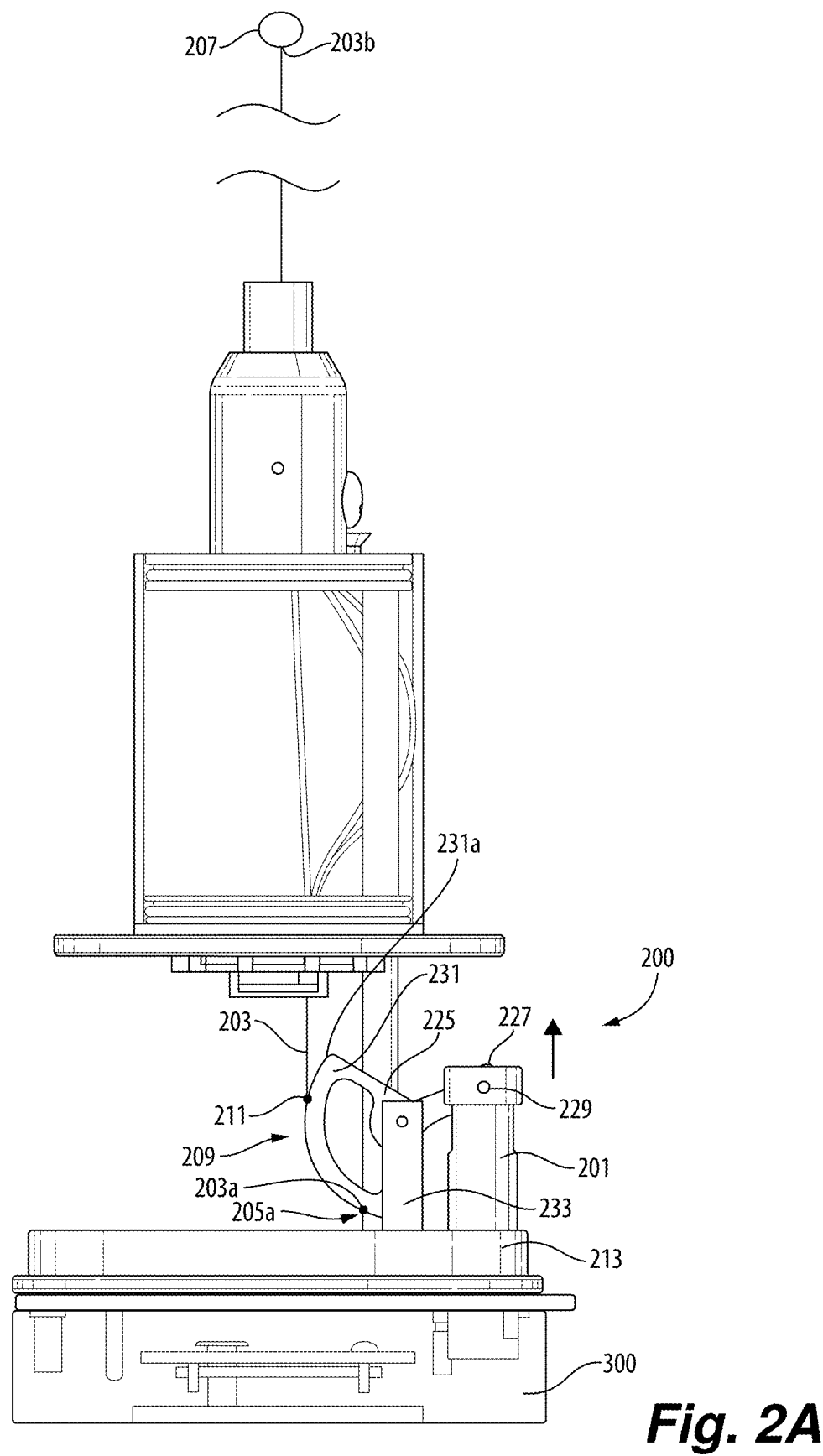
FIG. 2A illustrate another embodiment of a force transmission system in accordance with this disclosure, shown in a first position of actuation.
Figure 2B:
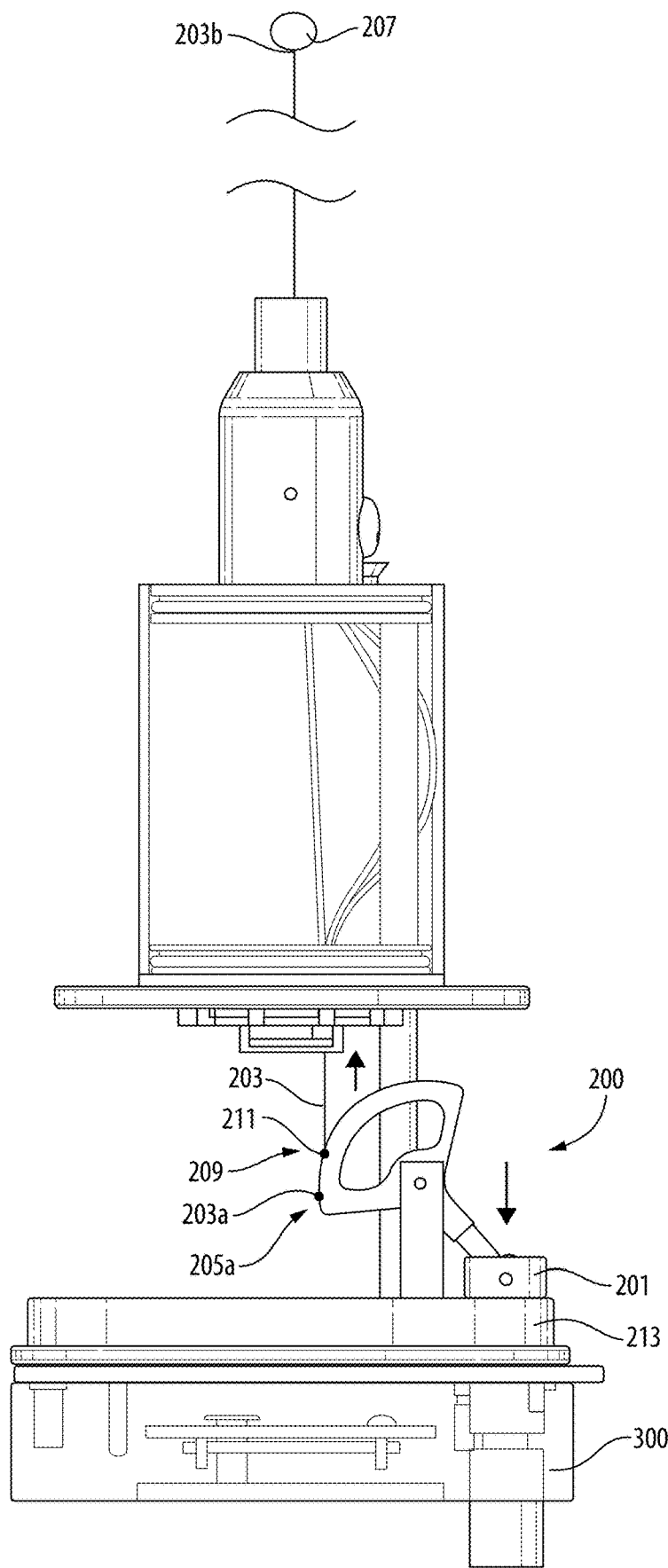
FIG. 2B illustrate the embodiment of FIG. 2A, shown in a second position of actuation.

In accordance with at least one aspect of this disclosure, referring to FIGS. 1A-2B, a force transmission system 100, 200 for a robotically controlled medical device can include a pushing actuator 101, 201 configured to be pushed by a robotic instrument controller (e.g., as disclosed in U.S. patent application Ser. No. 16/495,038, already incorporated by reference above) and a wire 103, 203. The wire 103, 203 can include a first end 103a, 203a attached to an end 101a of the pushing actuator 101 to be pushed distally (e.g., upward as shown in FIG. 1A) by the pushing actuator 101 (e.g., as shown in the embodiment of FIG. 1A), or attached to a location 205a that moves with movement of the pushing actuator 201 (e.g., as shown in the embodiment of FIGS. 2A-2B). The wire 103, 203 can include a second end 103b, 203b attached to a distal location 107, 207 of the medical device (e.g., anchored within a steerable assembly to cause steering of a shaft of the medical device).

The system 100 can include a reverse motion device 109, 209 that can be interfaced with the wire 103, 203 between the first end 103a, 203a and the second end 103b, 203b. The reverse motion device 109, 209 can be configured to cause a proximal pulling action on the second end 103b, 203b in response to pushing of the first end 103a distally by the pushing actuator 101 or other actuation (e.g., as shown in FIGS. 2A and 2B) by the pushing actuator 201. The reverse motion device 109, 209 can be configured to maintain a point of contact 111, 211 with the wire 103, 203 in the same spatial location (e.g., a fixed point relative to the base 113, 213 of an instrument adapter 300 of the robotically controlled medical device) to prevent wire motion (e.g., radial movement) due to actuation.

In certain embodiments, as shown in FIGS. 1A, 1B, 1C, and 1D, the reverse motion device 109 can be one or more pulleys 115, 117 mounted radically and axially fixed to a base 113 (e.g., via a frame 119). The one or more pulleys 115, 117 can be interfaced with the wire 103 (e.g., such that the pulleys 115, 117 roll when the wire 103 is actuated). The pushing actuator 101 can be configured to move axially relative to the base 113 (e.g., along direction A shown) to push the wire 103 (e.g., distally).

In certain embodiments, the one or more pulleys 115, 117 can include a first pulley 115 and a second pulley 117 configured to reverse direction of the wire 103. In certain embodiments, the first pulley 115 can be inserted within a slot 121 (e.g., defined in the direction of pushing motion, e.g., direction A as shown) of the pushing actuator 101 to cause the wire 103 to contact the first pulley 115 such that the wire 103 is parallel and/or coaxial with a pushing axis (e.g., coaxial with the straight portion of the wire 103. The second pulley 117 can be sized and/or positioned to contact the wire 103 to be coaxial with a proximal direction axis (e.g., coaxial with the wire 103 shown in FIGS. 1A-1C, e.g., parallel with direction B). The second pulley 117 can be larger than the first pulley 115, e.g., as shown. In certain embodiments, the reverse direction of the wire 103 can be 180 degrees, e.g., as shown.

In accordance with at least one aspect of this disclosure, a force transmission system 100 for a robotically controlled medical device can include a pushing actuator 101 configured to be pushed by a robotic instrument controller, and one or more pulleys 115, 117 mounted relative to the pushing actuator 101. The system 100 can include a wire 103 having a first end 103a attached to an end 101a of the pushing actuator 101 to be pushed distally by the pushing actuator 101, and a second end 103b attached to a distal location 107 of the medical device. The wire 103 can be interfaced with the one or more pulleys 115, 117 to cause a proximal pulling action on the second end 103b in response to pushing of the first end 103a distally.

In certain embodiments, e.g., as shown in FIG. 2, the reverse motion device 209 can be a reverse linkage 225 attached to the pushing actuator 201 on a first end 227 (e.g., at pin 229) and interfaced with a wire 203 on the second end 231. The reverse linkage 225 can be rotatably mounted and axially fixed to a base 213 (e.g., via frame 233). The second end 231 of the reverse linkage 225 can be or include a curved contact surface 231a to maintain the point of contact 211 with the wire 203 in the same spatial location to prevent wire motion due to actuation. Any other suitable reverse actuation mechanism is contemplated herein.

Embodiments can include instrument force transmission mechanisms for robotically controlled medical instruments. Embodiments can include a reverse motion design using two fixed pulleys instead of linkages, or a linkage that has a curved surface, for engaging one or more control wires of the medical device. A medical device can include any suitable number of force transmission systems (e.g., one for each control wire).

A robotically controlled medical instrument can include an adapter having one or more embodiments of a force transmission mechanism in accordance with this disclosure. Any suitable robotically controlled medical device (e.g., robotically controlled jaws or blades) is contemplated herein.

In accordance with at least one aspect of this disclosure, a robotically controlled medical device can include a steerable elongate member and a hub (e.g., connected to the steerable elongate member. The medical device can include a force transmission system disposed in the hub. The force transmission system can be or include any suitable force transmission system disclosed herein, e.g., as described above.

Any module(s) disclosed herein can include any suitable hardware and/or software module(s) configured to perform any suitable function(s) (e.g., as disclosed herein, e.g., as described above). As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A force transmission system for a robotically controlled medical device, comprising:
    a pushing actuator configured to be pushed by a robotic instrument controller;
    a wire having:
        a first end attached to an end of the pushing actuator to be pushed distally by the pushing actuator or attached to a location that moves with movement of the pushing actuator; and
        a second end attached to a distal location of the medical device; and
    a reverse motion device interfaced with the wire between the first end and the second end, the reverse motion device being configured to cause a proximal pulling action on the second end in response to pushing of the first end distally by the pushing actuator or other actuation by the pushing actuator, wherein the reverse motion device is configured to maintain a point of contact with the wire in the same spatial location to prevent wire motion due to actuation.

2. The system of claim 1, wherein the reverse motion device comprises one or more pulleys rotatably mounted and axially fixed to a base, the one or more pulleys interfaced with the wire, wherein the pushing actuator is configured to move axially relative to the base to push the wire.

3. The system of claim 2, wherein the one or more pulleys include a first pulley and a second pulley configured to reverse direction of the wire.

4. The system of claim 3, wherein the first pulley is inserted within a slot of the pushing actuator to cause the wire to contact the first pulley such that the wire is parallel and/or coaxial with a pushing axis.

5. The system of claim 4, wherein the second pulley is sized and/or positioned to contact the wire to be coaxial with a proximal direction axis.

6. The system of claim 5, wherein the second pulley is larger than the first pulley.

7. The system of claim 6, wherein the reverse direction of the wire is 180 degrees.

8. The system of claim 1, wherein the reverse motion device comprises a reverse linkage attached to the pushing actuator on a first end and interfaced with a wire on the second end, wherein the reverse linkage is rotatably mounted and axially fixed to a base, wherein the second end of the reverse linkage is or includes a curved contact surface to maintain the point of contact with the wire in the same spatial location to prevent wire motion due to actuation.

9. A robotically controlled medical device, comprising:
    a steerable elongate member;
    a hub; and
    a force transmission system disposed in the hub, the force transmission system comprising:
        a pushing actuator configured to be pushed by a robotic instrument controller;
        a wire having:
            a first end attached to an end of the pushing actuator to be pushed distally by the pushing actuator or attached to a location that moves with movement of the pushing actuator; and
            a second end attached to a distal location of the medical device; and
        a reverse motion device interfaced with the wire between the first end and the second end, the reverse motion device being configured to cause a proximal pulling action on the second end in response to pushing of the first end distally by the pushing actuator or other actuation by the pushing actuator, wherein the reverse motion device is configured to maintain a point of contact with the wire in the same spatial location to prevent wire motion due to actuation.

10. The device of claim 9, wherein the reverse motion device comprises one or more pulleys rotatably mounted and axially fixed to a base, the one or more pulleys interfaced with the wire, wherein the pushing actuator is configured to move axially relative to the base to push the wire.

11. The device of claim 10, wherein the one or more pulleys include a first pulley and a second pulley configured to reverse direction of the wire.

12. The device of claim 11, wherein the first pulley is inserted within a slot of the pushing actuator to cause the wire to contact the first pulley such that the wire is parallel and/or coaxial with a pushing axis.

13. The device of claim 12, wherein the second pulley is sized and/or positioned to contact the wire to be coaxial with a proximal direction axis.

14. The device of claim 13, wherein the second pulley is larger than the first pulley.

15. The device of claim 14, wherein the reverse direction of the wire is 180 degrees.

16. The device of claim 10, wherein the reverse motion device comprises a reverse linkage attached to the pushing actuator on a first end and interfaced with a wire on the second end.

17. The device of claim 16, wherein the reverse linkage is rotatably mounted and axially fixed to a base.

18. The device of claim 17, wherein the second end of the reverse linkage is or includes a curved contact surface to maintain the point of contact with the wire in the same spatial location to prevent wire motion due to actuation.

* * * * *